(12) United States Patent
Kramer

(10) Patent No.: US 6,869,569 B2
(45) Date of Patent: Mar. 22, 2005

(54) APPARATUS FOR DIFFERENTIATING BLOOD CELLS USING BACK-SCATTER

(75) Inventor: Donald L. Kramer, Boca Raton, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 10/828,586

(22) Filed: Apr. 21, 2004

(65) Prior Publication Data

US 2004/0197232 A1 Oct. 7, 2004

Related U.S. Application Data

(62) Division of application No. 10/227,010, filed on Aug. 23, 2002, now Pat. No. 6,743,634.

(51) Int. Cl.[7] .......................... G01N 33/48; G01N 31/00
(52) U.S. Cl. .................. 422/73; 422/82.01; 422/82.02; 422/82.05; 422/82.09; 436/63; 436/8; 436/10; 436/164; 436/149; 436/150; 435/2
(58) Field of Search ............................... 422/73, 82.01, 422/82.02, 82.05, 82.09; 436/63, 8, 10, 164, 149, 150; 435/2

(56) References Cited

U.S. PATENT DOCUMENTS

| | | | |
|---|---|---|---|
| 3,835,315 A | * | 9/1974 | Gravitt, Jr. .................. 250/574 |
| 4,702,598 A | | 10/1987 | Bohmer |
| 4,882,284 A | | 11/1989 | Kirchanski et al. |
| 4,914,310 A | * | 4/1990 | Jarofski ...................... 250/574 |
| 4,939,081 A | | 7/1990 | Figdor et al. |
| 5,017,497 A | | 5/1991 | Gerard de Grooth et al. |
| 5,125,737 A | | 6/1992 | Rodriguez et al. |
| 5,155,044 A | | 10/1992 | Ledis et al. |
| 5,686,308 A | | 11/1997 | Li et al. |
| 6,025,201 A | | 2/2000 | Zelmanovic et al. |

(List continued on next page.)

FOREIGN PATENT DOCUMENTS

JP 02-207034 7/2002

OTHER PUBLICATIONS

Eisert, W.G., "Cell Differentiation Based on Absorption and Scattering", *The Journal of Histochemistry and Cytochemistry*, vol. 27, No. 1, pp. 404–409 (1979).

Sloot, et al., "Elastic Light Scattering from Nucleated Blood Cells: Rapid Numerical Analysis", *Applied Optics*, vol. 25, No. 19, Oct. 1, 1986.

Sloot, et al., Scattering Matrix Elements of Biological Particles Measured in a Flow Through System: theory and Practice:, *Applied Optics*, vol. 28, No. 10, May 15, 1989.

Ault, K. A., "Flow Cytometric Measurement of Platelet Function and Reticulated Platelets", *Annals New York Academy of Sciences*, 677:293–308 (1993).

Primary Examiner—Maureen M. Wallenhorst
(74) Attorney, Agent, or Firm—Warren W. Kurz; Mitchell E. Alter

(57) ABSTRACT

Blood cells of interest are readily distinguishable from other blood cells and look-a-like particles found in a blood sample by their back-scatter signature. A preferred method for differentiating platelets in a blood sample is to irradiate the cells and particles, one at a time, with a beam of radiation, and to detect back-scattered (reflected) radiation using a plurality of optical fibers to transmit the back-scattered radiation to a high-gain photodetector, e.g. a photomultiplier tube. Preferably, the back-scatter signal so obtained is combined with a second signal representing, for example, either the level of forward-scatter within a prescribed, relatively narrow angular range, or the level of side-scattered radiation, or the level of attenuation of the cell-irradiating beam caused by the presence of the irradiated cell or particle in the beam, or the electrical impedance of the irradiated cell or particle, to differentiate the cells of interest. The method and apparatus of the invention are particularly useful in differentiating platelets and basophils in a blood sample.

15 Claims, 12 Drawing Sheets

U.S. PATENT DOCUMENTS

| | | | |
|---|---|---|---|
| 6,137,108 A | * 10/2000 | DeThomas et al. | 250/339.07 |
| 6,210,969 B1 | 4/2001 | Li et al. | |
| 6,214,625 B1 | 4/2001 | Li et al. | |
| 6,228,652 B1 | 5/2001 | Rodriguez et al. | |
| 6,232,125 B1 | 5/2001 | Deka et al. | |
| 6,743,634 B2 | * 6/2004 | Kramer | 436/63 |

* cited by examiner

APPARATUS FOR DIFFERENTIATING BLOOD CELLS USING BACK-SCATTER

RELATED U.S. APPLICATION DATA

Division of U.S. application Ser. No. 10/227,010, filed Aug. 23, 2002, now U.S. Pat. No. 6,743,634, issued Jun. 1, 2004, entitled "Method and Apparatus for Differentiating Blood Cells Using Back-Scatter."

FIELD OF THE INVENTION

The present invention relates to methods and apparatus for differentiating various types of blood cells on the basis of their respective light-scatter signature. More particularly, it relates to a method and apparatus for differentiating blood cells, and especially platelets and basophils, on the basis of their back-scatter signature.

BACKGROUND OF THE INVENTION

The use of light scattering measurements as a means for differentiating various types of small particles is well known. For example, in virtually all sophisticated hematology instruments, it is common to measure the forward light scattering properties of blood cells by passing the cells, one at a time, through the interrogation zone of an optical flow cell. While in the interrogation zone, each cell is irradiated by a laser beam, and one or more photodetectors, strategically positioned forward of the interrogation zone, operate to sense the level of forward scattered radiation, often within several different predetermined angular ranges. In addition to measuring forward light scatter, some hematology instruments measure side scatter as well, using a separate photodetector located orthogonally of the irradiated cell. These light scattering measurements are often combined with other simultaneously made measurements to better differentiate cell types of particular interest from other cells and other particulate material within the sample that have similar light-scattering properties within the angular ranges measured. These other simultaneously-made measurements include those representing the cell's physical volume, its electrical conductivity, and its effectiveness in attenuating the irradiating beam by virtue of its presence in the beam (sometimes referred to as the axial light loss (ALL) of a cell). Having made various cell parameter measurements, the instrument then produces scattergrams in which the different parameters measured are plotted against each other. Ideally, each sub-population of cells of the same type appears in these scattergrams as a tight cluster of data points, each point representing an individual cell, and each cluster being readily identifiable from other clusters by a clearly identified spacing between the clusters. In such case, it is a simple matter to "gate" cells of one cluster from those of another cluster and to enumerate the cells of each type within the gate. Unfortunately, this ideal is sometimes difficult to realize since, for many reasons, a small percentage of cells of one type invariably invade the spatial domain of cells of other types, thereby making the cell count of a cell type of interest somewhat imprecise. As noted below, this is especially true in the case of platelet and basophil differentiation.

In an article entitled "Flow Cytometric Measurement of Platelet Function and Reticulated Platelets," by Kenneth A. Ault, Annals New York Academy of Sciences, 677:293–308 (1993), the importance of platelet analyses for clinical applications is discussed. This article also discusses the problem of identifying and enumerating platelets using conventional light-scattering techniques. It is noted that the concentration of platelets in a normal whole blood sample is relatively high, being second only to the concentration of red blood cells (erythrocytes). One milliliter of blood normally contains about 250 million platelets. Thus, while they are about 20 times less frequent than red cells, platelets are about 25 times more frequent than all types of white cells (leukocytes) combined. While their normal size range (1 to 4 microns) enables platelets to be readily identified from other types of normal cells in a blood sample, their cluster in a scattergram usually contains a large amount of cellular debris (fragments of all cells) that "look like" platelets in terms of their normally measured volume and forward light scattering properties. Ault notes an uncertainty in differentiating platelets from cell debris on the basis of forward and side-scatter measurements alone, and he describes a more reliable technique based on both forward light scatter and fluorescence measurements. While the light scatter/fluorescence technique described by Ault does provide a more positive identification of platelets than the noted light scatter alone technique, this technique requires the additional step of selectively tagging or labeling platelets with fluorescent dye molecules, either directly or via suitable monoclonal antibodies that have been tagged with a fluorescent marker. This tagging step, of course, is both time-consuming and costly. Further, this tagging of platelets subjects the platelets to considerable agitation or manipulation, which has an undesired effect on platelet activation.

In U.S. Pat. No. 6,025,201 to D. Zelmanovic et al., several different techniques for differentiating and counting platelets are noted. The patent disclosure is directed to a method for assessing the activation state of platelets by determining their respective dry mass and refractive index. A preferred method comprises the steps of measuring the forward light-scatter of platelets irradiated by a laser beam within two different light scatter ranges, a low range of between 1 and 7 degrees, and a high range of between 5 and 20 degrees. Alternatively, the forward light-scatter measured within one of the two preferred scatter ranges is combined with a DC volume measurement, and a Mie Scattering Theory-based analysis is performed to provide platelet counting and analysis. This platelet analysis scheme is considered advantageous over the above-noted Ault technique in that it lends itself to full automation, requiring no off-line sample preparation for fluorescent tagging purposes. The same can be said, of course, for the many different fully-automated platelet analysis techniques used commercially to date. These techniques include (a) the total impedance scheme (used in the Model STKS™ and Model GEN•S™ blood analyzers manufactured and sold by the assignee hereof) where platelet volume is determined by monitoring the change in electrical impedance of a restricted aperture caused by a platelet passing through it; (b) the total light-scatter scheme (used in the TECHNICON H* System instrument made and sold by Bayer, and in the ORTHO ELT-8 instrument made and sold by Ortho Diagnostics) where the intensity of forward scattered light is monitored within one or more angular ranges, such scatter intensity being proportional to platelet volume; and (c) the combined impedance and light scatter scheme used in the Cell-Dyn® 4000 blood analyzer made and sold by Abbott Laboratories) where cell volume is determined both electrically (via aperture impedance) and optically (via forward light scatter) simultaneously. As indicated above, however, all of these schemes are susceptible to cross-contamination by non-platelets, introducing a certain degree of uncertainty in the data reported. The impedance approach is problematic in that any cell debris having a volume similar to that of a normal platelet will be displayed and counted as a platelet. The forward scatter approach is problematic in that cellular debris of the same size or volume as a platelet will produce a forward-scatter signature similar to a platelet and thereby be counted as a platelet. Further, in making such light scatter measurements, it is common to use relatively large surface area photodetectors (typically pin diodes) to collect the scattered light. Unfortunately, such large detectors are problematic in that they also collect stray light reflected by various surfaces within the optical system and thereby produce signals having a relatively low signal-to-noise ratio. Even when shaped to exclude the collection of stray light (e.g., shaped as a circular ring centered about the irradiating beam axis), these photodetectors still require a substantial surface area to achieve the gain necessary to sense the scattered radiation, and the larger the surface area, the slower the electrical response time. Schemes that combine the electrical and optical techniques are subject to the same disadvantages of each approach. Further, they are disadvantageous in that apparatus must be provided for making both electrical and optical measurements.

As regards conventional techniques for identifying and quantifying the basophil sub-population of white cells in a blood sample, uncertainties can arise in the numbers reported not only because of the very small number of these cells in the sample (being substantially less than one per cent of the leukocyte population) but also because of their similarity in physical and electrical properties with the relatively plentiful monocyte and lymphocyte sub-populations. Typically, a combination of forward-angle light-scatter, and RF conductivity, and DC impedance measurements are made to differentiate basophils from other cell types, as is the case in the STKS™ and GEN•S™ Blood Analyzers, made and sold by Beckman Coulter, Inc. Alternatively, forward angle measurements have been combined with polarized side-scatter measurements to differentiate basophils, as is the case in the Cell-Dyn hematology instruments made and sold by Abbott Laboratories. Neither technique can be said to be optimum. The former is disadvantageous as requiring an RF circuit for establishing a high-frequency current flow through the cell-interrogation zone, whereby changes in the current through the zone, as occasioned by the passage of blood cells and/or particles of differing impedance characteristics, can be monitored. Both techniques are problematic in that the optical coupling efficiency between the light-scattering particle and the large surface area detectors commonly used to detect the scattered light is low.

It has been suggested that multiple bundles of fiber optics, arranged in concentric rings, can be used to optically couple scattered radiation from a scatter plane to multiple photodetectors (e.g., photomultiplier tubes and photodiodes) remotely spaced from the scatter plane. See, "Cell Differentiation Based on Absorption and Scattering" by Wolfgang G. Eisert, The Journal of Histology and Cytochemistry, Vol.27, No.1, pp404–409 (1979). As described by Eisert, optical fibers are arranged so that their respective light-collecting ends form five concentric rings centered about a centrally located light-collecting bundle of optical fibers. The respective distal ends of the individual fibers of each of the five concentric rings are optically coupled to five different photomultiplier tubes, and the distal ends of the individual fibers of the center bundle are optically coupled to a photodiode. The center bundle of fibers is optically aligned with the beam axis, and the other bundles, with their individual fibers being arranged in a circle, are also arranged parallel to the beam axis. Thus, each ring of fibers collects scattered light in a discrete angular range determined by the diameter of the fiber (or the width of the rings), the radial displacement of the fiber end relative to the beam axis (i.e., the diameter of the ring), and the axial spacing of the fiber ends from the scattering light source. The sixth and center bundle of fiber optics, being positioned on the beam axis, serves to monitor the axial light loss of the beam, as occasioned by the passage of cells therethrough.

In the fiber-optic light coupler proposed by Eisert above, the respective light-collecting ends of all the fibers are disposed in a common plane that is arranged perpendicular to the optical axis of the cell-irradiating light beam. Thus, it will be appreciated that, due to the numerical aperture of the fibers, the optical coupling of scattered light into the optical fibers deteriorates as the scatter angle increases. Additionally, as the scatter angle increases, the angle of incidence between the scattered light and the fiber end increases, thereby increasing the number of internal reflections required to transmit the scattered light from one end of the fiber to the other end. This problem of coupling efficiency is exacerbated by the dramatic reduction in scatter intensity at relatively large scatter angles.

In addition to forward- and side-scatter measurements, it has been suggested that back-scatter (i.e., reflected light) measurements may prove useful in differentiating blood cell types. In a theoretical paper entitled, "Elastic Light Scattering From Nucleated Blood Cells: Rapid Numerical Analysis," by Sloot and Figdor, Applied Optics, Vol. 25, No. 19, 1 Oct. 1986, it is noted that simultaneous detection of the light-scatter intensities in the forward lateral, and backward directions is required to optimize the detection of different cell types in heterogeneous populations of nucleated blood cells. Here, a model is presented to calculate the light-scattering properties of nucleated blood cells which are mimicked by two concentric spheres. It is derived from the calculations presented (no actual measurements on cells were made) that the back-scatter intensity is determined by the nucleus/cytoplasm ratio and changes in the optical density of the cytoplasm and nucleus. The analysis presented strongly suggests a direct correlation between the transparency of the nucleus and the intensity of the back-scatter signal. While no hardware is disclosed in this paper for making any light-scattering measurements at all, a subsequent paper, "Scattering Matrix Elements of Biological Particles Measured in a Flow Through System: Theory and Practice" by Sloot et al., Applied Optics, Vol. 28, No. 10, 15 May 1989, alludes to the use of large surface area scatter detectors and the need to apply "large cone integration" to account for the relatively large surfaces. This paper schematically illustrates a back-scatter detector having a central aperture through which the particle-irradiating laser beam travels before irradiating the particle. Upon striking the particle, the large surface of the back-scatter detector collects and detects back-scattered light through a large cone angle, i.e., throughout a large angular range. As noted above large surface area detectors, while advantageous from the standpoint of optical gain, are highly disadvantageous from a response-time standpoint. As the detector surface area increases, the detector response time decreases, thereby limiting the speed at which the system can resolve cells.

SUMMARY OF THE INVENTION

In view of the foregoing discussion, an object of this invention is to provide a more effective method for differentiating blood cells from other particles and cells in a blood sample.

Another object of this invention is to provide an improved apparatus for differentiating and counting blood cells of interest in a blood sample.

In accordance with the present invention, it has been found that certain blood cell types, notably platelets and basophils, are readily distinguishable from cellular debris and other look-a-like cells and particles found in a blood sample by their respective back-scatter signature (i.e., their ability to reflect radiation in the general direction of the irradiating source). Preferably, this back-scatter signature is determined by optically coupling the back-scattered radiation to a high-gain photodetector via a plurality of optical fibers. To differentiate platelets, this back-scatter information is preferably combined with (e.g., plotted against) other information simultaneously obtained from the irradiated particles, for example, the particle's effectiveness in attenuating the irradiating beam by virtue of its presence in the beam (i.e., its axial light loss (ALL) parameter) or the particle's effectiveness in scattering light either in a forward plane at a certain prescribed angle, or sideways. To differentiate basophils, the back-scatter information is preferably combined with side-scattered information obtained from the irradiated particles. Alternatively, the cells can be differentiated by combining the back-scatter information from each cell with information representing the cell's volume or its electrical conductivity.

Thus, a preferred method for differentiating blood cells in a blood sample containing both platelets and non-platelet particles comprises the steps of (a) passing the individual particles of the blood sample, one at a time, through a cell-interrogation zone in which each cell is irradiated by a beam of radiation; (b) simultaneously (i) detecting the level of back-scattered radiation from each irradiated particle through a plurality of optical fibers positioned to optically couple the back-scattered radiation to a high-gain photodetector, and (ii) detecting the level of another measurable effect produced by the particle passing through the cell-interrogation zone; (c) producing first and second signals proportional to the respective levels of the detected back-scattered radiation and the other measurable effect; and (d) using the first and second signals to differentiate blood cells of interest from other cells and particles in the blood sample. As indicated above, the other measurable effect of the irradiated particle includes the level of forwardly scattered light within a certain angular range, the level of side-scattered light, the amount of light loss in the irradiating beam caused by the presence of the irradiated particle in the beam, or a change in level of either a DC or an RF current passing through the interrogation zone occasioned by the passage of a cell through such zone.

According to another aspect of the invention, apparatus for differentiating blood cells of interest from other cells and particles in a blood sample comprises (a) an optical flow cell through which the individual particles of a blood sample can be made to pass, one at a time; (b) a light source for producing a beam of radiation for irradiating individual particles passing through the optical flow cell; (c) an optical detector positioned at a location to detect back-scattered light from an irradiated particle passing through the optical flow cell and for producing a first signal proportional to the level of back-scattered radiation detected; (d) a second detector positioned at a location to detect another measurable effect produced by a particle passing through the flow cell and for producing a second electrical signal proportional to the detected level of the other measurable effect; and (e) a logic and control unit for receiving the first and second electrical signals and for differentiating platelets from non-platelet particles based on the first and second electrical signals received. Preferably, the optical detector comprises: (i) a high-gain photodetector; (ii) a plurality of optical fibers, (iii) a first fiber optic holder for positioning the respective light-collecting ends of the optical fibers at a location to collect the back-scattered radiation from the irradiated blood cells or particles, and (iv) a second fiber optic holder for positioning the respective light-discharge ends of the fibers adjacent to the photodetector.

The invention and its advantages will be better understood from the ensuing detailed description of preferred embodiments, reference being made to the accompanying drawings in which like reference characters denote like parts.

DETAILED DESCRIPTION OF PREFERRED EMBODIMENTS

Figure 1:
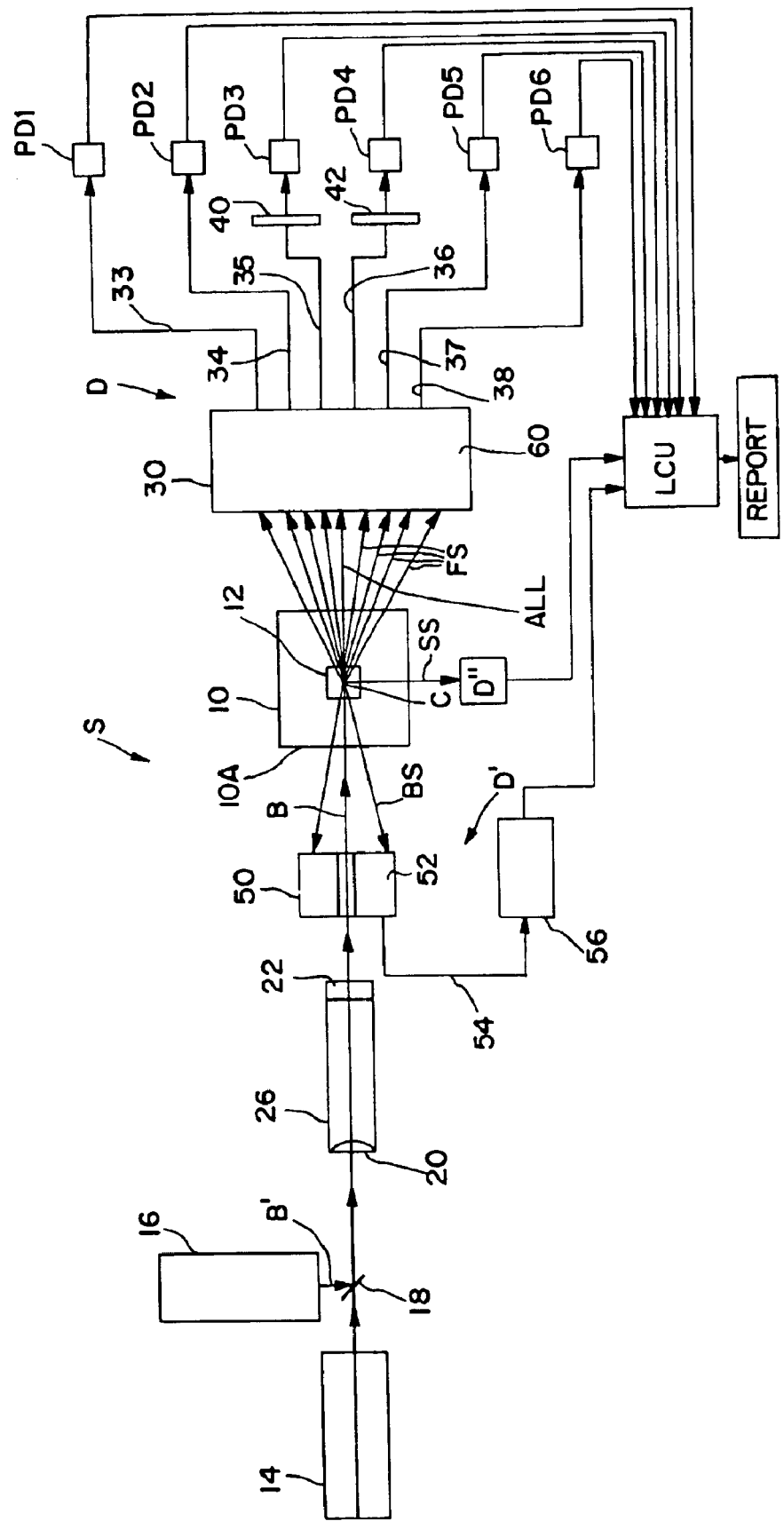
FIG. 1 is a schematic illustration of a portion of a system used to analyze blood cells and other small particles on the basis of the light-scattering signature of such cells and particles.

Referring now to the drawings, FIG. 1 schematically illustrates an electrooptical system S adapted to carry out the blood cell-differentiating method of the invention. System S is designed to be retro-fitted into a standard XL™ Flow Cytometer made and sold by Beckman Coulter, Inc. System S comprises a forward scatter/axial light-loss detector D, a back-scatter detector D' and a side-scatter detector D". The respective electrical output signals produced by these detectors are fed to and processed by a suitably programmed microprocessor of a Logic and Control Unit (LCU) comprising the flow cytometer instrument. Based on the instrument's programming, various particle parameters detected by detectors D, D' and D" are reported and displayed, e.g., as histograms and scattergrams, as presented below.

Central to system S is an optical flow cell 10 having a centrally located particle-interrogation zone 12 through which a stream of individual particles in suspension can be made to pass, one at a time, in a well known manner. The flow cell is optically transparent, preferably being fabricated from quartz, and the interrogation zone measures about 100×100 microns in transverse cross section. While passing through the interrogation zone, the individual particles are irradiated by a light beam B provided by a laser 14. Preferably, a second laser 16 is used to provide a second light beam B' that becomes co-linear with beam B after striking the 45 degree, semi-transparent mirror 18. Preferably, the two beams are of different wavelength, for example, one beam being red in color, as provided, e.g., by a helium-neon laser, and the other beam being blue in color, as provided, e.g., by an argon laser. Upon passing through a small aperture formed in the light-collecting optical system 50 comprising the back-scatter detector D' (described below), the beam(s) are brought into sharp focus at the center C of the particle-interrogation zone 12 by a pair of crossed cylindrical lens 20, 22 supported at opposite ends of a lens housing 26. When irradiated by the focused beam(s), each particle acts to scatter light in all directions according to a complex function based upon the wavelength of the irradiating light beam and certain particle characteristics, including size, refractive index, reflectivity, geometry, internal make-up, etc. Further, each irradiated particle acts to modulate the intensity of the irradiating beam(s), again depending on the physical and optical properties of the particle. Forward light scatter FS, i.e., the light scattered forwardly of the irradiated particle, as determined by the direction of propagation of the particle-irradiating beam, is detected within a plurality of different angular ranges by the forward-scatter/axial light-loss detector D, described in detail below. As its name indicates, detector D also operates, as described in detail below, to detect the axial light loss ALL occurring in the irradiating beam(s) as a result of the passage of a particle through the beam(s). Preferably, such axial light loss is detected at different wavelengths, as determined by the respective radiant outputs of lasers 14 and 16. Back-scattered light BS, i.e. light scattered backwardly or reflected from the irradiated particles toward the irradiating source, is detected within a predetermined angular range by the above-mentioned back-scatter detector D', described in detail below. Beam light scattered orthogonally to the direction of beam B is detected by the side-scatter detector D".

Figure 2:
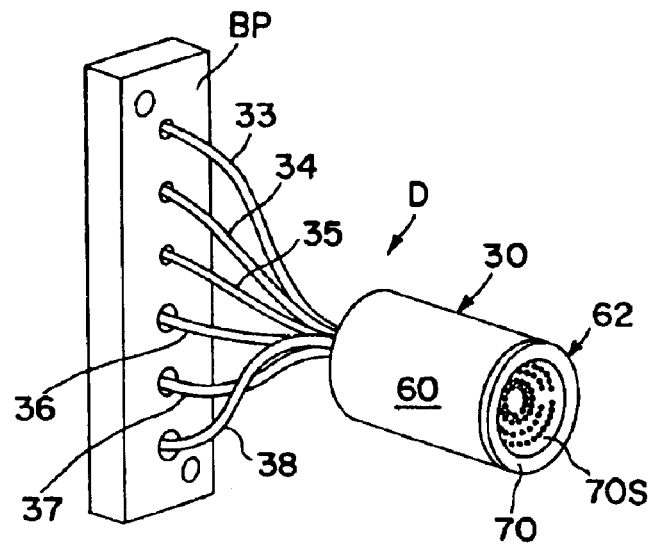
FIG. 2 is a perspective illustration of a portion of a forward light scatter detector forming a part of the preferred apparatus of the present invention.

Forward-Scatter/Axial Light-Loss Detector:

Referring to FIGS. 1 and 2, the forward-scatter/axial light loss detector D generally comprises (i) a pair of optical fiber holders 30, 30', (ii) a plurality of discrete fiber optic bundles 33–38 (illustrated as being six in number, though there may be more or less), and (iii) a like plurality of photodetectors PD1–PD6. Preferably, each of the photodetectors is a high-gain solid state device; however, each may be a photomultiplier tube. Each fiber optic bundle preferably comprises at least three or four optical fibers and may comprise upwards of fifty fibers, depending on the pattern in which they are arranged within the fiber holder 30, and the diameter of the fibers. Each optical fiber has a light-collecting end that, in use, is positioned by holder 30 to collect or receive radiant energy that is to be transferred by the fiber, via multiple internal reflections, to a relatively remote location, and an opposing light-discharge end that emits the collected and transmitted light. Referring to FIG. 2, a fiber optic holder 30' serves to support, in suitably sized holes arranged in a vertical array, the light-discharge ends of the six fiber optic bundles 33–38. The six photodetectors PD1–PD6 are also supported by holder 30' (on the rear side, as viewed in FIG. 2) in a position so that their respective light-sensitive faces are adjacent to the respective light-discharge ends of the optical fibers. Preferably, all of the individual fibers in the fiber optic bundles are the same in all respects except, perhaps, for length, which may vary slightly from bundle to bundle, depending on space constraints. Preferably, each fiber has a diameter of about 500 microns, and all fibers are made from a common optical material. Particularly preferred fibers are the SI Bare Fibers, sold by Boston Optical Fiber.

Figure 3:
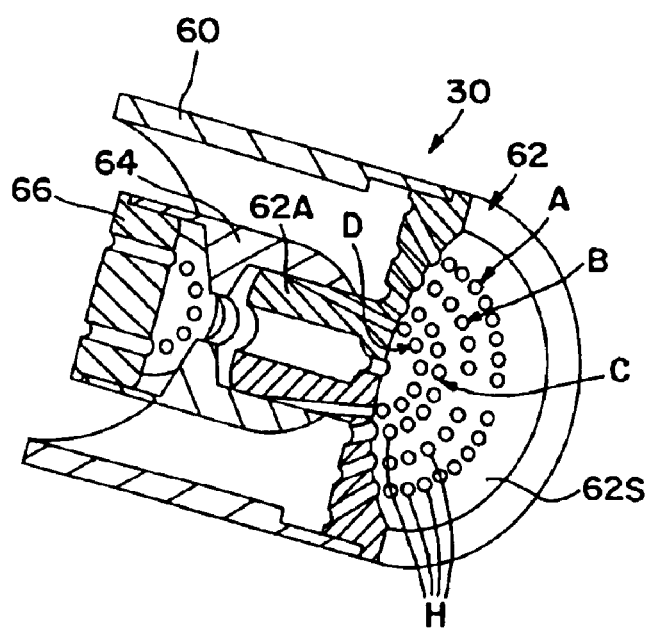
FIG. 3 is an enlarged perspective of a section of the light-gathering component of the FIG. 2 apparatus.
Figure 4:
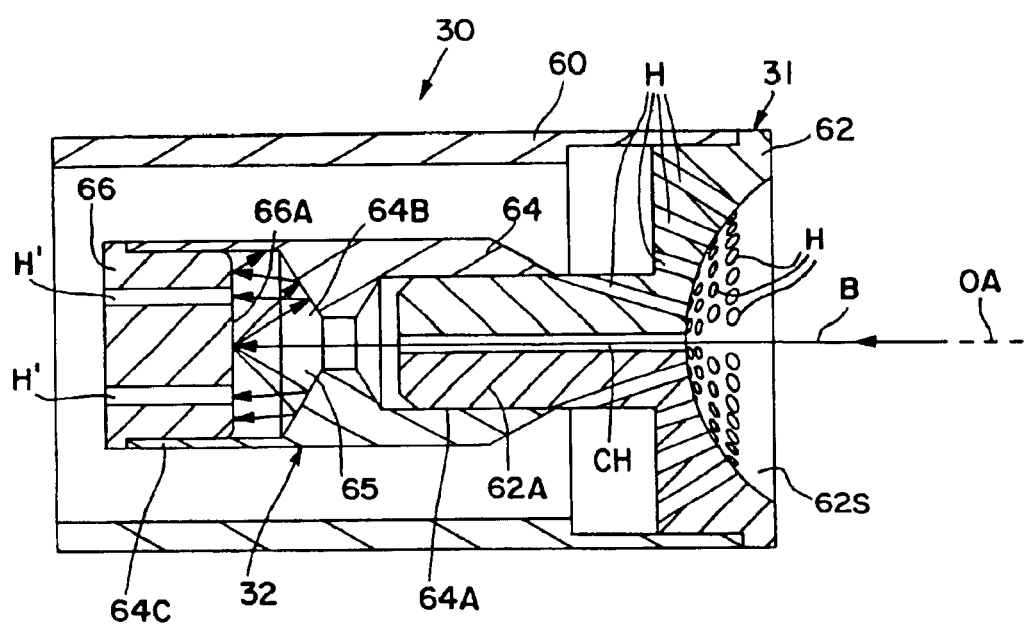
FIG. 4 is a sectional illustration of the FIG. 3 apparatus.

As best shown in FIGS. 3 and 4, optical fiber holder 30 comprises a cylindrical sleeve 60 that serves to support and contain two inter-connected components, namely, (1) a forward-scatter collecting component 31 that functions to support the respective light-collecting ends of four of the fiber optic bundles, 33, 34, 37, 38, in positions so that each bundle collects forwardly scattered light FS within one of four different angular ranges, and (2) an axial light-collecting component 32 that functions to support the light-collecting ends of the remaining two fiber optic bundles, 34, 35, in a position to collect axial light as modulated in intensity by particles in its path. Sleeve 60 is preferably made of plastic and has a diameter of about 12.5 mm. and a length of about 20 mm.

Forward Light-Scatter Collecting Component:

The forward light-scatter collecting component 31 of fiber optic holder 30 is positioned within sleeve 60 forwardly of the axial light-collecting component 32. Component 31 functions to hold the respective light-collecting ends of fiber optic bundles 33, 34, 37 and 38 so as to form four concentric rings A, B, C and D, respectively (shown in FIG. 5B). When the fiber optic holder is in use, each ring of fiber optic ends is centered about the optical axis OA of the irradiating beam(s) and functions to collect forwardly scattered light in a discrete angular range determined by the ring diameter, the axial spacing between the scattering source (the center of the flow cell) and the fiber end, and the diameter of the fiber. As described above, the light-discharge ends of the bundles 33, 34, 37 and 38 are optically coupled to photodetectors PD1, PD2, PD5 and PD 6 in such a manner that each photodetector receives light from only one bundle. Thus, the output of each photodetector reflects the intensity of forwardly scattered light within one of the four different angular ranges determined by the position in which the light-collecting ends of the fibers to which it is optically coupled.

Figure 5A:
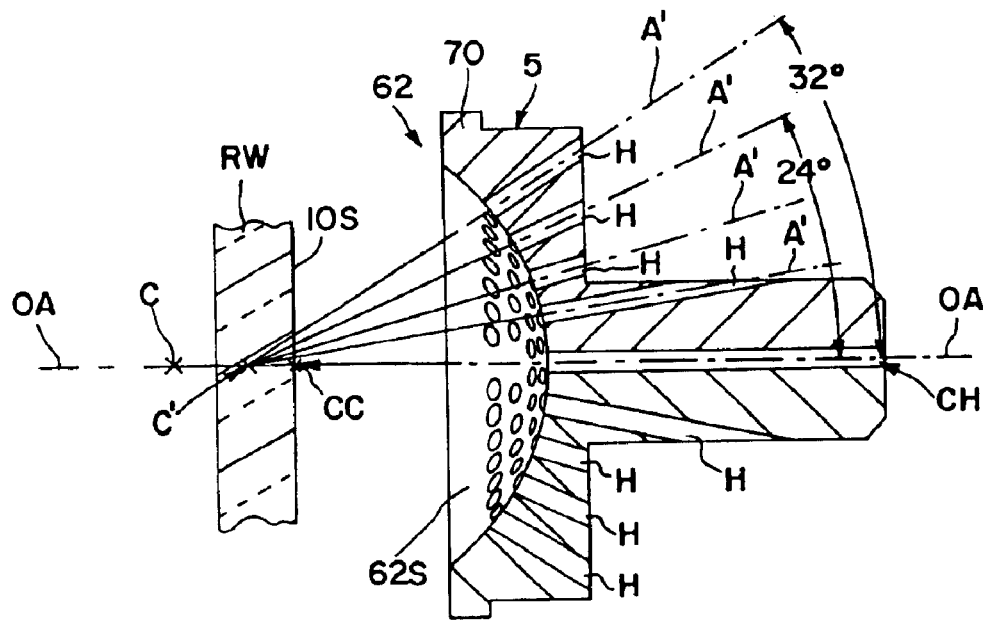
FIGS. 5A and 5B are cross-sectional and front plan views, respectively, of the primary fiber-optic holder component of the FIG. 3 apparatus.
Figure 5B:
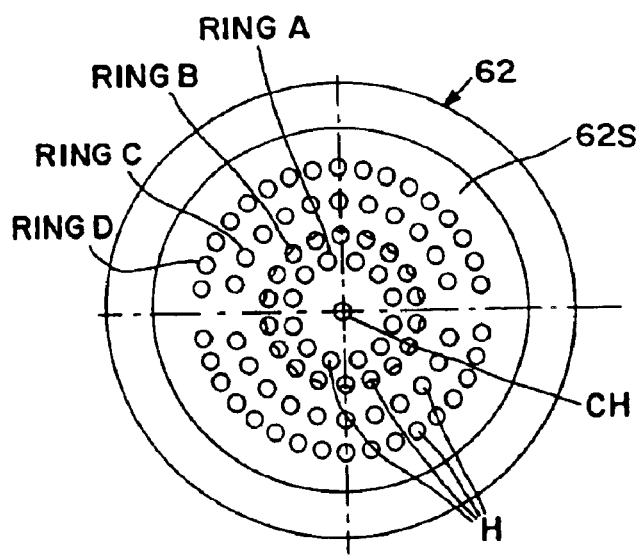

As best shown in FIGS. 3 and 4, the forward light-scatter collecting component 31 comprises a circular, fiber-holding plate 62 having a cylindrical stem portion 62A extending rearwardly from the central region of the plate. Preferably, plate 62 has a spherically concave front surface 62S in which a plurality of fiber-supporting bore holes H are drilled to form the above-noted pattern of four concentric rings A, B, C and D. The circular pattern of bore holes H are centered about a central bore hole CH that extends axially through the entire length of stem 62A. Each bore hole H is intended to receive and appropriately position a light-collecting end portion of one of the optical fibers of the fiber optic bundles 33, 34, 37 and 38. Note, the center bore hole CH is not intended to receive an optical fiber and serves only to transmit axial, non-scattered, beam light to the axial light collecting component 32, described below. Each bore hole H has a diameter slightly exceeding the nominal diameter (500 microns) of a single optical fiber it is intended to receive. Preferably, each bore supports the light-collecting end portion of one optical fiber so that (a) the light-collecting end of the supported fiber portion is substantially co-planar with the concave surface 62S, and (b) the longitudinal optical axis of the supported fiber points directly at the "apparent" position of the light scattering source, i.e., the virtual position of the scattering source taking into account the refractive properties of the transparent rear wall of the flow cell through which scattering is viewed by the light-collecting fiber ends. By this arrangement, scattered light will enter the respective light-collecting ends of the supported fiber portions in a direction substantially parallel to the fiber axes A' and will thereby be most efficiently coupled into the respective fiber interiors for transmission to the associated photodetectors. As best shown in FIGS. 5A and 5B, the fiber-supporting bore holes H pass completely through plate 62, thereby enabling the fiber ends to enter the bore holes from the rear surface of plate 62 and be suitably fixed to the plate (e.g., by epoxy). Preferably, each bore hole H is of a length to provide axial support to the fiber end portion it contains for a distance of at least 2 mm from the fiber's light-collecting end.

Referring to FIG. 5A, plate 62 is shown in a position in which the center of curvature CC of surface 62S is located at the rear surface 10S of the optical flow cell 10. Viewing the flow cell center C (where the scattering source is nominally located) through the optically transparent (quartz) rear wall RW of the flow cell, the flow cell center C actually appears to be located at a point C', inside the flow cell wall. Thus, in drilling holes H, it is preferred that their respective axes A' (which are coincident with the axes of the supported fibers) converge at point C'. In the preferred embodiment, the radius of curvature of surface 62S is about 0.25 inches, and the apparent position of the flow cell center is about 0.030 inches further away from surface 62S, inside the flow cell wall.

Figure 10:
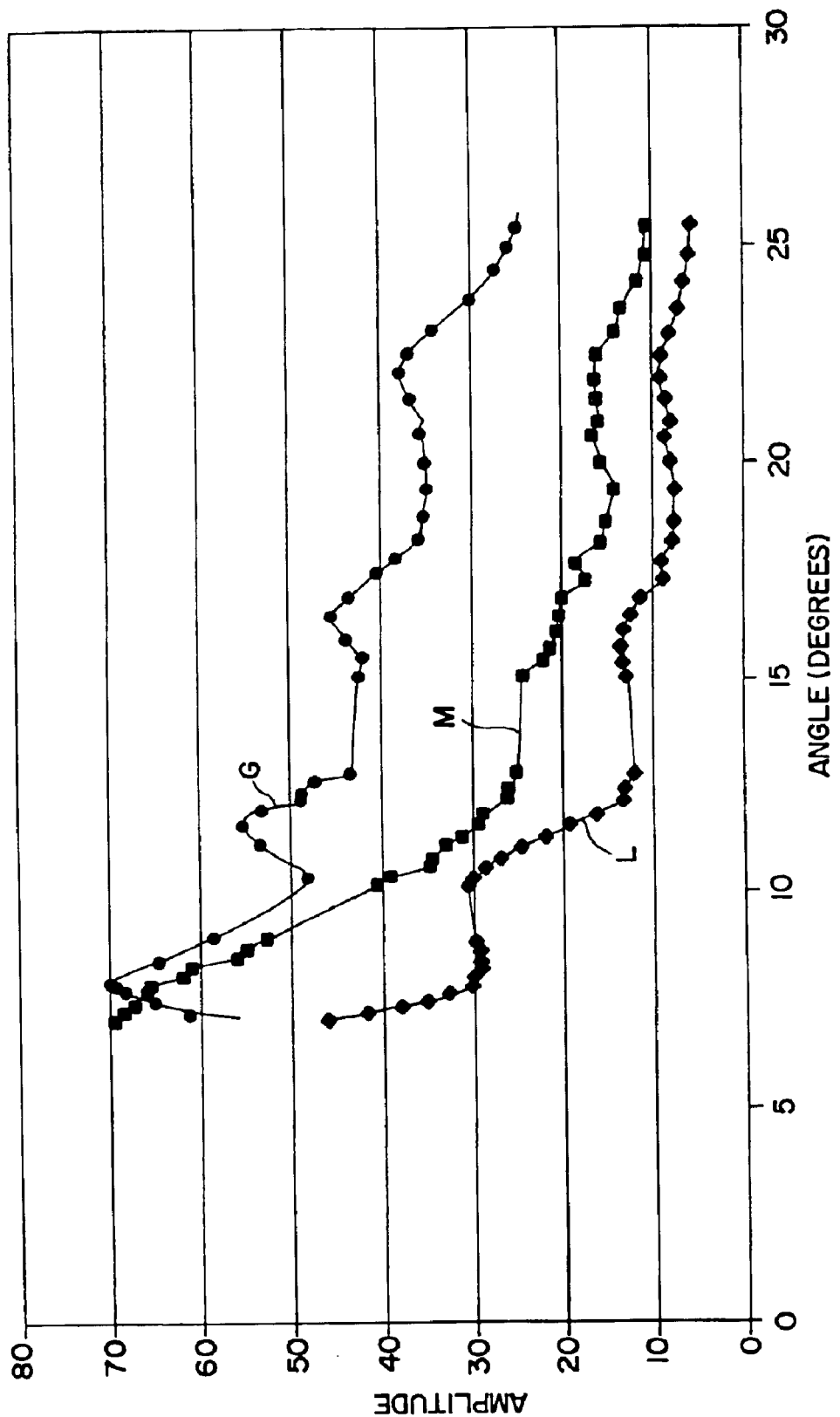
FIG. 10 illustrates the forward light-scattering characteristics of lymphocytes, monocytes and granulocytes.

As indicated above, each ring of bore holes in surface 62A supports the optical fibers of one of the fiber optic bundles 33, 34, 37 and 38. Thus, referring to FIG. 5B, the twelve bore holes of ring A, for example, support a total of twelve optical fibers, as may constitute the number of fibers of fiber optic bundle 33. Similarly, the thirty-four bore holes of ring D can support a total of 34 fibers, as may constitute the number of fibers in fiber optic bundle 38. Obviously, the diameter of the rings determines the number of optical fibers that can be accommodated. The nominal angle at which forward light scatter is detected is determined by the diameter of each ring, as determined by a centerline passing through the respective axes of the bore holes, and the axial distance of the ring from the scattering source. The angular ranges through which scatter is detected is determined by the diameter of each fiber, assuming there is a single fiber in each bore hole. According to a particularly preferred embodiment of the invention, the diameter of fiber optic rings A, B, C, and D and the radius of curvature of surface 62A are chosen so as to provide nominal forward scatter angles of 11 degrees, 16 degrees, 24 degrees and 32 degrees. Referring to FIG. 10 in which the intensity (amplitude) of forward scatter as a function of angle is plotted for the three major sub-populations of leukocytes (namely lymphocytes L, monocytes M and granulocytes G), it will be appreciated that the preferred angles of approximately 11 degrees, 16 degrees and 24 degrees provide for a relatively good displacement of the three curves; thus, in a scattergram in which any two of the forward scatter angles are plotted against each other, the three sub-populations of leukocytes will be readily identified. A radius of curvature of about 6.2 mm. for surface 62A, and a fiber diameter of 500 microns provides an angular range, centered about these angles, of about plus or minus 2 degrees.

Figure 6A:
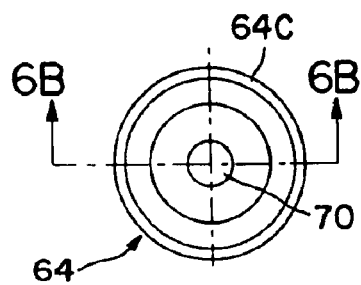
FIGS. 6A and 6B are front plan and cross-sectional views, respectively, of the axial light reflector component of the FIG. 3 apparatus.
Figure 6B:
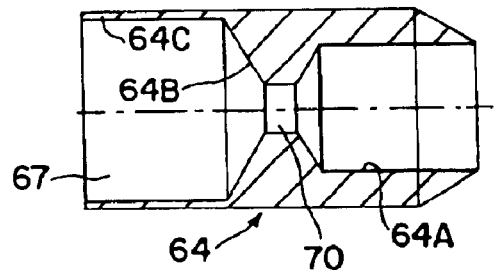
Figure 7A:
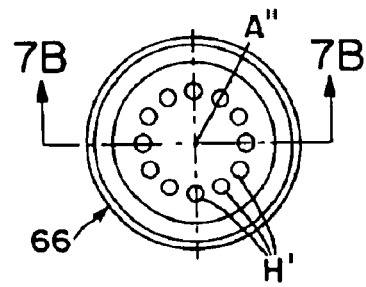
FIGS. 7A and 7B are front plan and cross-sectional views, respectively, of the axial light diffuser/secondary fiber optics holder component of the FIG. 3 apparatus.
Figure 7B:
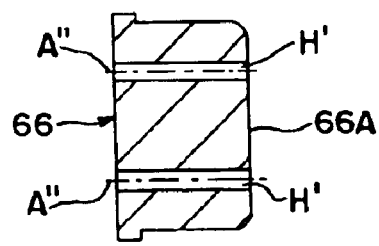

Axial Light Collecting Component:

The axial light collecting component 32 of fiber optic holder 32 operates both to (1) support the respective light-collecting ends of one or more fiber optic bundles in a position to receive axial beam light for transmission to remotely positioned photodetector(s) and (2) prevent such beam light from being retro-reflected back towards the back-scatter detector D' where it would otherwise interfere with the collection and detection of the relatively low-level back-scatter signal. In preventing retro-reflection of beam light, component 32 functions to diffuse the beam light prior to collecting it for transmission and detection. Referring to FIGS. 4, 6A and 6B, component 32 comprises a cylindrically-shaped housing 64 having a central, cylindrically-shaped opening 64A in its forward end. The stem portion 62A of plate 62 is press fit into opening 64A and thereby provides support for housing 64. The rear portion of housing 64 has a conically-shaped internal wall 64A having a reflective surface. Wall 64A defines, in part, a light-reflecting chamber 65. A circular flange 64C extending rearwardly from housing 64 defines a cylindrical opening 67 that supports an axial plug 66 (shown in FIGS. 7A and 7B) that serves as a secondary fiber optic holder. A small, centrally located opening 69 in housing 64 provides communication between openings 64A and 67. The axial plug 66 is provided with a planar light-diffusing top surface 66A, preferably made of Delrin®, a trademark of E. I. DuPont. A circular pattern of bore holes H' is formed in plug 66, such holes being parallel to each other and to the central longitudinal axis of the plug. These bore holes are adapted to receive optical fibers, preferably alternating around the circular pattern from either of the fiber optic bundles 35 or 36 shown in FIGS. 1 and 2. The optical fibers from bundles 35 and 36, are positioned within the bore holes H' so that their respective light-collecting ends are co-planar with the light-diffusing surface 66A. Thus, as illustrated in FIG. 4, an axial light beam B passing through the central bore hole CH formed in stem 62A and through the central opening 69 in member 64 will strike the light-diffusing surface 66A of plug 66. The incident beam light is thus diffused in all directions, and the diffused light is reflected multiple times within the reflection chamber 65 until a portion of the reflected light strikes the light-collecting ends of the optical fibers supported by plug 66. Axial beam light is thus collected and transmitted to photodetectors PD3 or PD4. Owing to (a) the relatively small diameter (about 1 mm) of the central bore hole CH, (b) the length (about 12 mm) of the central bore hole CH, and (c) the light-diffusing effect of surface 66A, minimal beam light is reflected back towards the optical flow cell and the back-scatter detector D' that might interfere with the detection of both forward and back-scattered light. Preferably, a pair of color absorption filters 40 and 42 is positioned between the light-discharge ends of fiber optic bundles 35 and 36, respectively, and the light-sensitive surfaces of photodetectors PD3 and PD4 for the purpose of differentiating axial light loss at two different wavelengths, e.g. in the event beam B is polychromatic (as is the case when two different lasers are used to irradiate the particles).

Back-Scatter Detector

Figure 8A:
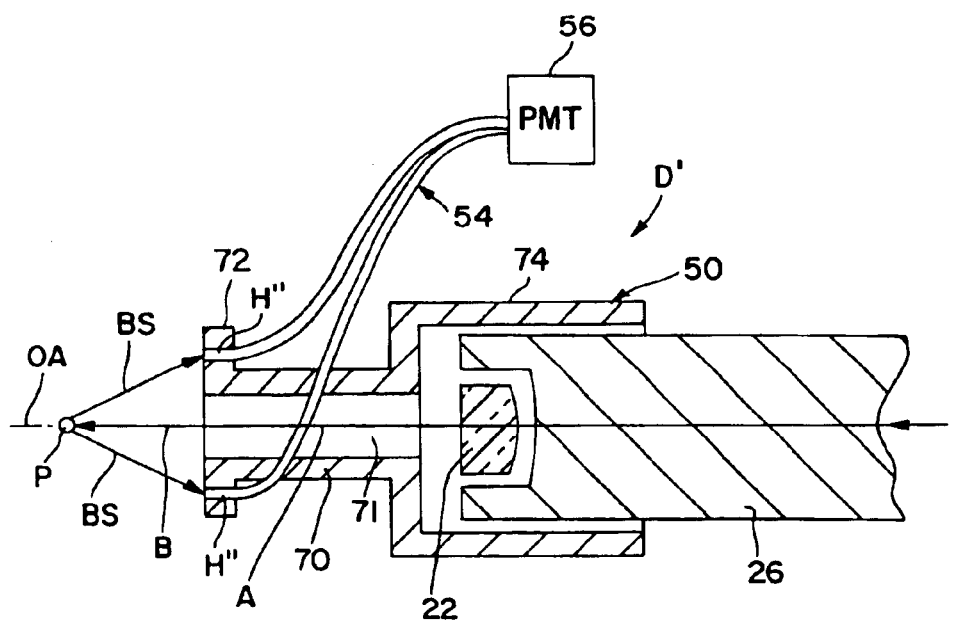
FIGS. 8A and 8B are cross-sectional and front plan views, respectively, of a preferred back-scatter detector comprising the FIG. 1 apparatus.
Figure 8B:
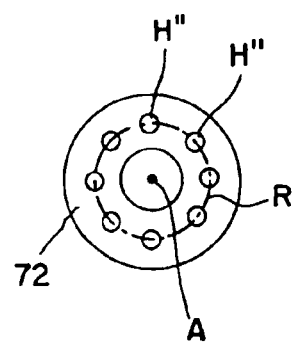

Referring to FIGS. 1, 8A and 8B, the back-scatter detector D' comprises a fiber optic holder 50, a bundle of optical fibers 54 and a photodetector 56. The optical fibers are preferably the same as those described above, and the photodetector is a conventional photomultiplier tube (PMT). The optical fiber holder 50 is preferably made of black plastic, most preferably Delrin plastic, a product of E.I. DuPont. Holder 50 comprises a relatively tiny central tubular portion 70 having a central bore 71 extending along its entire length. The central tubular potion 60 is provided with a circular, fiber-holding flange 72 at one end, and an enlarged tubular portion 74 at its opposing end. Preferably, the central tubular portion 70 has a length of about 2.5 mm., and an outside diameter of about 1.5 mm. The diameter of bore 71 is about 1.3 mm, sufficiently large to pass the particle-irradiating beam(s) B so that it can irradiate a particle P after passing through the bore. The enlarged tubular portion 74 has a length of about 4.0 mm., an outside diameter of about 3.3 mm. and an inside diameter of about 3.0 mm. The inside diameter of portion 74 is adapted to fit snugly over the end of lens housing 26, whereby the lens housing provides total support for the fiber optic holder 50.

As best shown in FIG. 8B, the circular flange 72 is provided with a plurality of bore holes H", each having a diameter adapted to receive and retain the light-collecting end portion of an optical fiber of the type described above; thus, each hole H" has a diameter slightly exceeding the 500 micron fiber diameter. The bore holes H' are arranged in a circular pattern to form a ring R centered about the central longitudinal axis A of the holder 50. Note, in use, axis A is coincident with optical axis OA. Preferably, ring R has a diameter of about 1.75 mm. Based on the anticipated spacing between the end of flange 62 (which is intended to abut the front face 10A of the flow cell 10) and the scattering source (i.e., the center of flow cell), this ring diameter provides a nominal back-scatter angle between about 2 degrees and 24 degrees; and the 500 micron fiber diameter provides an angular range of about 2 degrees (centered about the nominal back-scatter angle). A preferred nominal back-scatter angle is about 7 degrees, although ample signal strength has been detected at back-scatter angles as high as 24 degrees. Due to the relatively small area of the respective light-collecting ends of the optical fibers, the fibers collect relatively little stray laser light reflecting from various surfaces (e.g. the faces of the optical flow cell) located between the forward-scatter detector and the back-scatter detector. Thus, through the use of optical fibers, the signal-to-noise level of photodetector 56 is maintained relatively high compared to the non-directional large-area prior art detectors that collect, in addition to the back-scatter signal of interest large amounts of back-scattered light from sources other than the cells of interest.

Figure 9A:
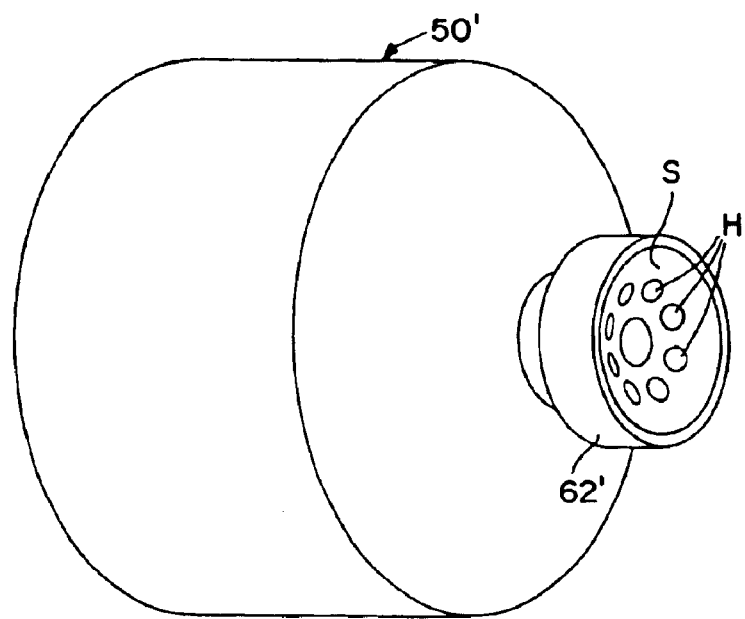
FIGS. 9A and 9B are perspective and cross-sectional illustrations, respectively, of another preferred back-scatter detector.
Figure 9B:
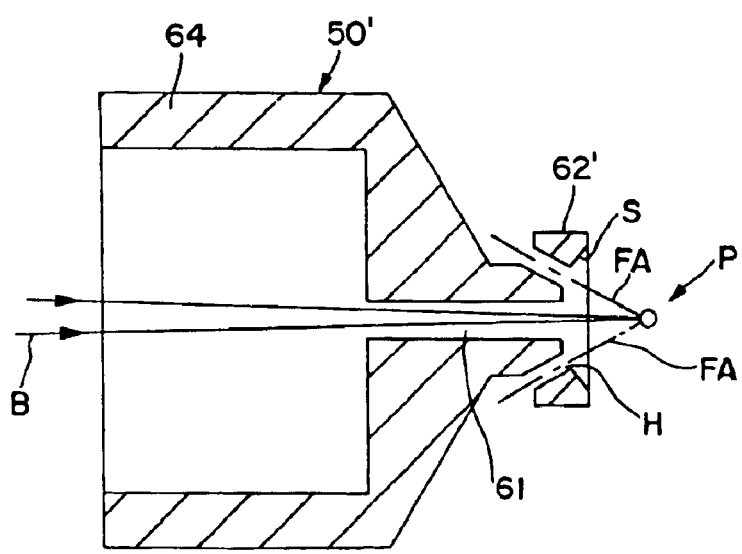

In the embodiment shown in FIG. 8A, it will be seen that the light-collecting end portions of the optical fibers are supported so that each fiber axis extends substantially parallel to the axis A of holder 50. In FIGS. 9A and 9B, another, more preferred, embodiment of the invention is shown in which a fiber holder 50' serves to support the fiber end portions so that their respective axes FA converge at a point P that represents the apparent position of the scattering source, i.e., the virtual position as viewed through the refractive front face of the flow cell. Here, a modified flange 72' is provided in which the fiber-containing bore holes H are formed (drilled) in a spherically-concave surface S. By this arrangement, the back-scattered light from the irradiated particle enters the light-collecting ends of the fibers from a direction that is substantially parallel to the fiber axis FA. Thus, optical losses due to multiple internal reflections within the fibers are reduced. This is especially advantageous in light of the relatively low-intensity back-scatter received from the particles.

Side-Scatter Detector

The side-scatter detector D" is conventional in design, preferably being of the type used in the aforementioned XL™ Flow Cytometer sold by the assignee hereof. Such detector generally comprises a lens system (not shown) for collecting side-scattered light SS (shown in FIG. 1) emerging from the lateral wall of the flow cell 10 and for focusing such light, upon collimating it, onto a photodetector. The lens system is closely spaced to the flow cell wall and accepts side scattered light over a relatively broad angular range, e.g., 90 degrees, plus or minus 45 degrees. Further details of the side-scatter detector can be had by referring to the commercially available instrument and its operating manual.

From the above discussion, it is apparent that each cell in a blood sample can be characterized by many different combinations of measurements made using the above-described detectors. For example, a cell's back-scattering characteristics can be plotted against its forward scatter characteristics within four different angular ranges provided by the four concentric rings A, B, C, D of fiber optics to provide four different scattergrams. Similarly, backscatter can be plotted against axial light loss at two different wavelengths, as well as against side-scatter. Obviously, each of the individual parameters or characteristics can be plotted against any of the other parameters measured. Of course, not all of the resulting scattergrams will prove useful in differentiating cells of interest from other cells and debris in a blood sample; however, it has been found that the backscatter signature of platelets in particular, and basophils to a lesser extent, when combined with certain other simultaneously measured parameters, is very useful in differentiating these particular cell types.

Referring to FIGS. 11–16, FIG. 11 is a typical scattergram obtained from an XL Flow Cytometer that has been retrofitted with a forward scatter detector of the type described above. In this case, the platelet sub-population was selectively tagged with a fluorescent dye (FITC) that is readily detectable by the instrument's fluorescence-detecting component. By plotting the forward scatter (FS) measurement made at 11 degrees by fiber optic ring B against the fluorescence (FL) measurement, it is apparent that the platelet sub-population P is readily differentiated from the cell debris D, as well as the main population of red blood cells (RBC) and a relatively small secondary red blood cell population RBC-2 having platelets attached. As noted above, this immunophenotyping technique for differentiating platelets, though accurate, is costly in terms of time and materials.

Figure 11:
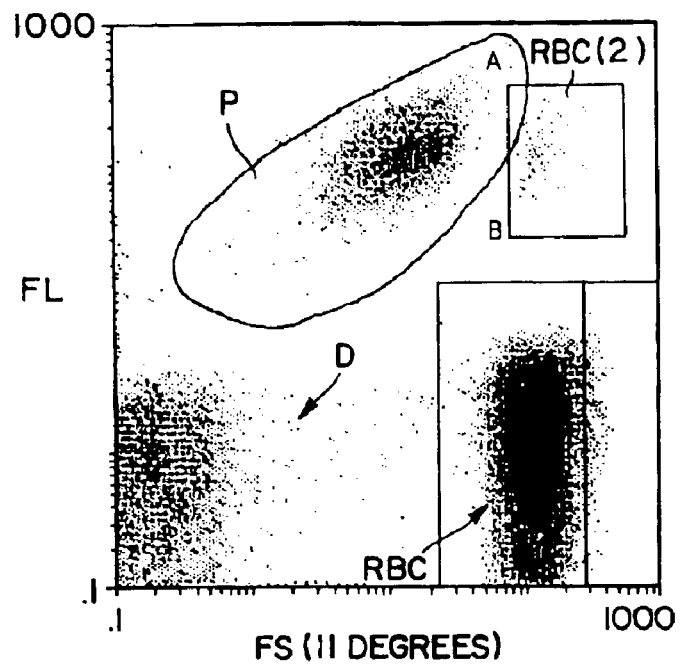
FIGS. 11 is a scattergram illustrating the results of an immunophenotyping technique for positively identifying cells of interest.
Figure 12:
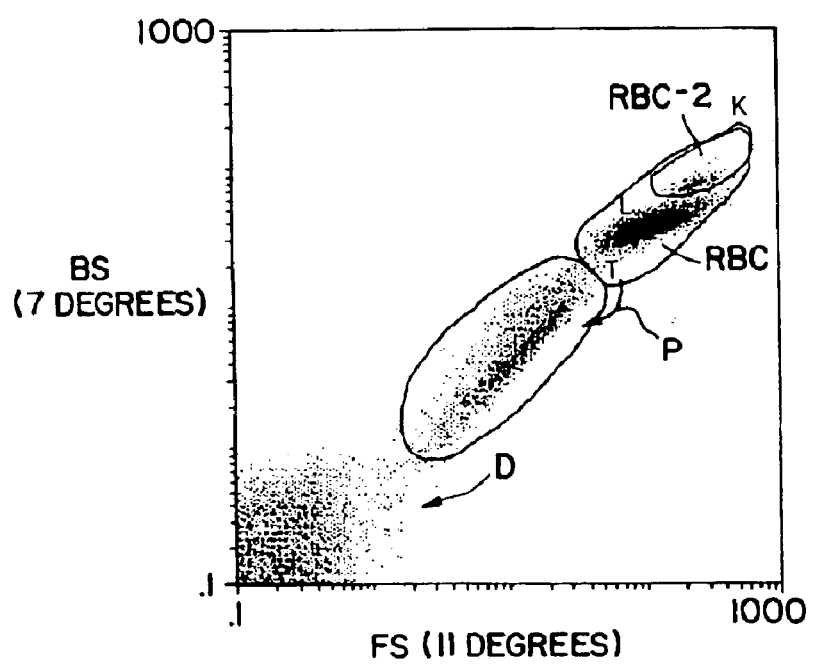
FIG. 12 is a scattergram illustrating the results of a light-scattering technique for identifying cells of interest.
Figure 13:
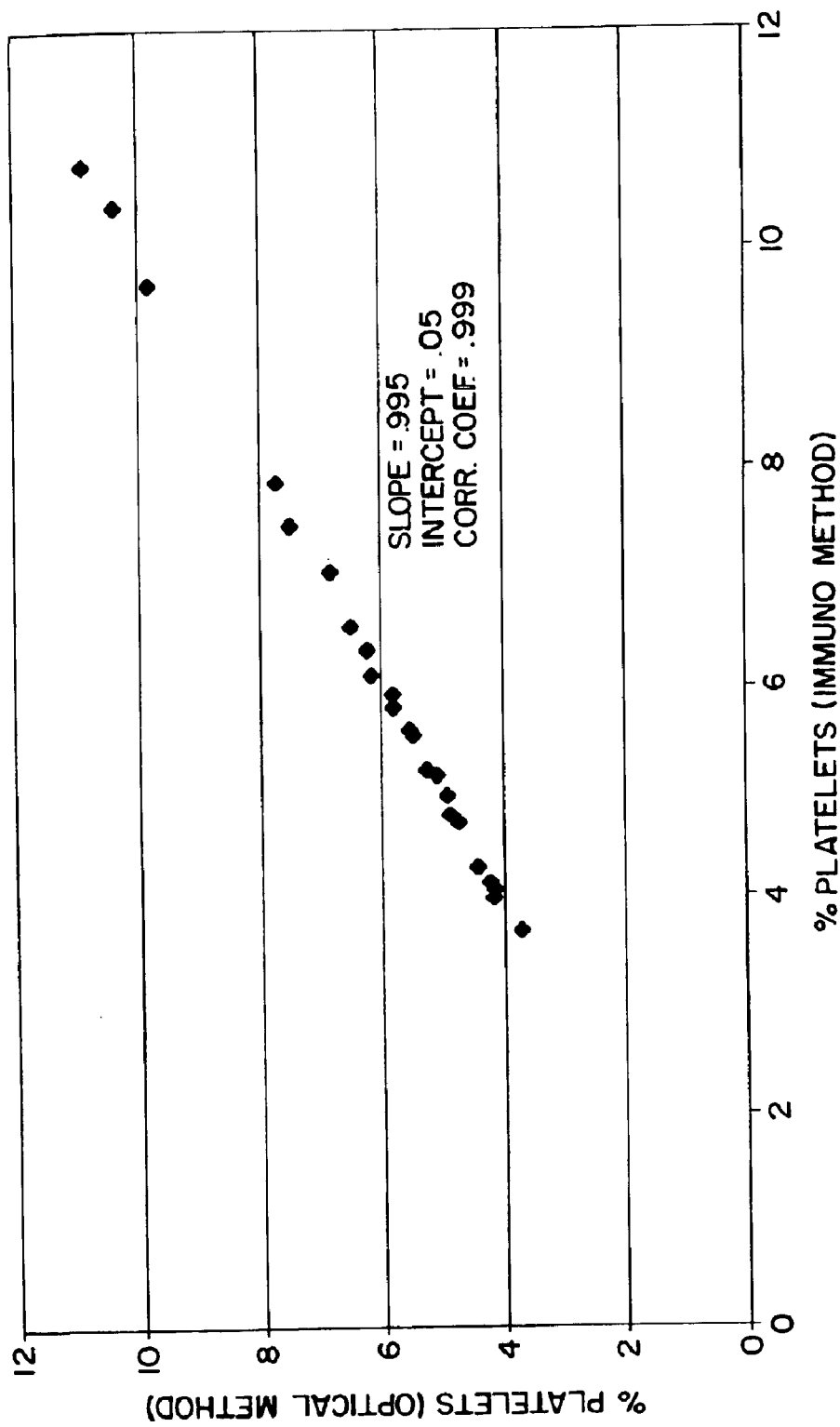
FIG. 13 is a graph illustrating the correlating of the techniques referred to in FIGS. 11 and 12.

Referring now to the scattergram of FIG. 12, the result of plotting the measured back-scatter (BS) parameter (i.e., the output of detector D') against the same forward-scatter parameter as used in FIG. 11 is shown for a single blood sample. As shown, the platelet sub-population P is readily distinguishable from the cellular debris D and the RBC sub-populations making it a simple matter to determine the percentage of platelets in the processed blood sample. As shown in FIG. 13, this optical-only method for differentiating platelets correlates extremely well with the more complex immunophenotyping method for differentiating platelets. In FIG. 13, the percentage of platelets found in a total of twenty-four different diluted blood samples are shown, each being determined simultaneously by the optical method described above (i.e. BS vs. FS at about 11 degrees) and by the standard immunophenotyping method (FL vs. FS, also at about 11 degrees). The correlation coefficient was determined to be an impressive 0.999.

Figure 14:
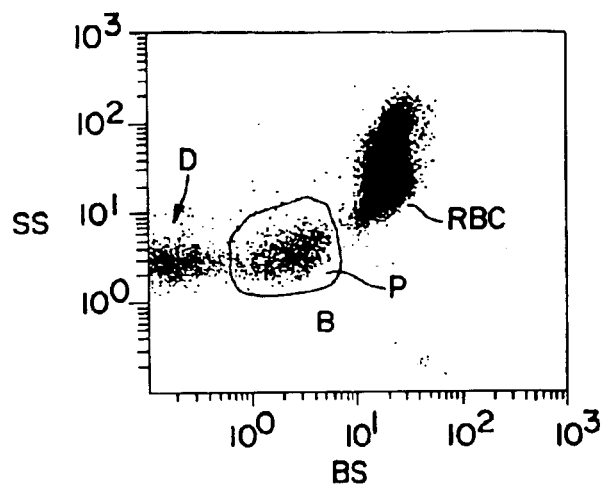
FIGS. 14–17 are scattergrams illustrating the results of combining different cell parameters determined by the apparatus of the invention.
Figure 15:
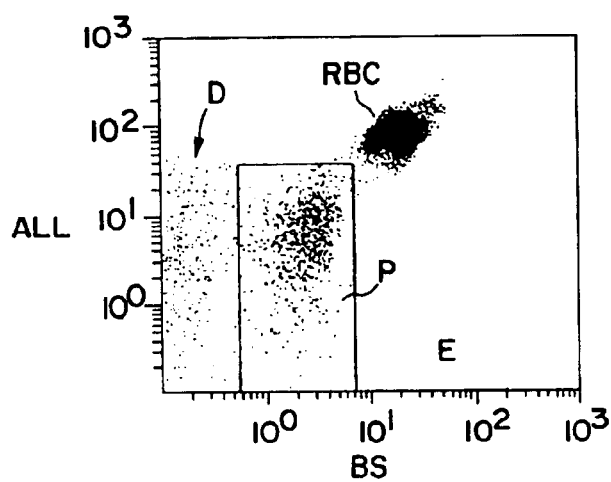
Figure 16:
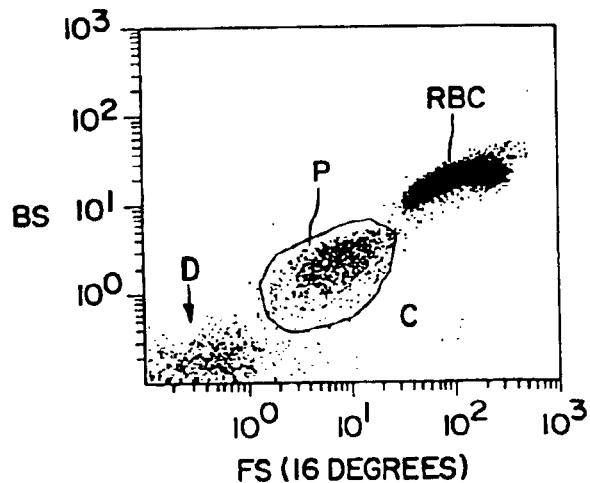

While the back-scatter parameter is a particularly useful tool to identify platelets when plotted against forward-scatter measurements made at about 11 degrees, it has also been found to be highly useful to identify platelets when plotted against side-scatter (SS), axial light loss (ALL), and forward scatter within other angular ranges, e.g. those centered about 16 degrees. Scattergrams illustrating the results of these combinations of parameters are shown in FIGS. 14–16, respectively. Clearly, in all these scattergrams, the platelet sub-population is readily distinguished from the cellular debris that has contaminated the results of conventional methods.

In using the above-described apparatus to provide the scattergrams discussed above, 1 milliliter of saline, preferably IsoFlow™ diluent made and sold by the assignee hereof, is added to I microliter of whole blood. A portion of the diluted sample of whole blood is then processed by an XL Flow Cytometer that has been retrofitted with detectors D and D' described above. To compare the results with the immunoassay "standard", the diluted sample may be incubated with a fluorescent antibody solution containing CD41/CD61. About 10,000 particles or cells are individually irradiated to produce forward-, side- and back-scatter information from the detectors D, D' and D". As described above, axial light loss (ALL) information is also provided by the forward-scatter detector D. At the same time, fluorescence data may be obtained on the stained platelets to positively identify them.

Figure 17:
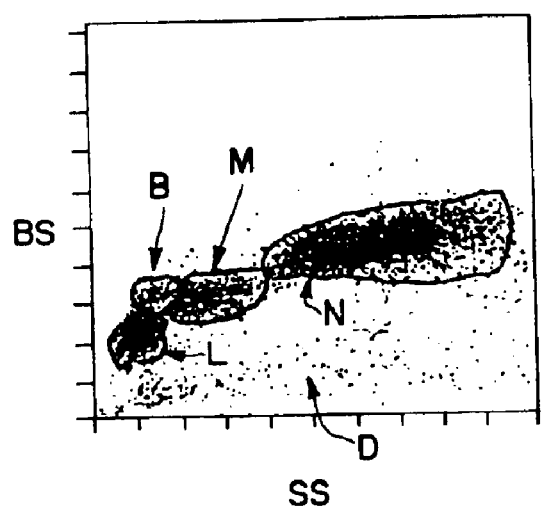

With regard to the detection of the basophil sub-population of white cells, the method and apparatus of the invention has been found to be capable of identifying them with the same degree of certainty as conventional methods when the back-scatter signature of these cells is plotted against their side-scatter signature. In FIG. 17, the back-scatter (BS) versus side-scatter (SS) scattergram shows a small discrete cluster of basophils (B) separated from the often contaminating clusters of monocytes (M) and lymphocytes (L). Also shown is the neutrophil sub-population (N) and cellular debris (D). The basophil data correlates fairly well with fluorescence vs. side-scatter data obtained on the same sample using a CD203c antibody to fluorescently stain the basophil sub-population.

In producing the scattergram of FIG. 17, 100 microliters of whole blood were mixed in a vial with 20 microliters of CD203c antibody tagged with a fluorescent dye (PE). This mixture was then incubated in the dark for 15 minutes at room temperature. After such incubation, the vial was placed into a Q-Prep™ Cell Processor, made and sold by Beckman Coulter, Inc., for lysis and fixation. The lysed and fixed sample was then washed three times and the cells were re-suspended in 500 microliters of phosphate-buffered saline (PBS). Immediately thereafter, the sample was processed by an XL Flow Cytometer that was retrofitted with the above-described back-scatter detector D'.

From the foregoing, it will be appreciated that a relatively simple light-scattering technique has been disclosed that is particularly useful in differentiating platelets and basophils in a blood sample. Cell-identification by using a cell's back-scatter parameter together with other purely optical parameters (e.g. light-scattering and axial light-loss parameters) is particularly advantageous over conventional systems requiring both optical and electrical impedance measurements, or optical and fluorescence measurements. By using a back-scatter detector of the type disclosed in a multi-parametric optical flow cell of the type disclosed in the commonly-assigned U.S. Pat. No. 6,228,652 issued to Rodriguez et al., DC and RF impedance measurements using the Coulter Principle, can be made simultaneously. The resulting BS vs. Z (impedance) scattergrams may prove useful in even better differentiating other types of blood cells.

While the invention has been disclosed with reference to particularly preferred embodiments, it will be appreciated that various modifications can be made without departing from the spirit of the invention, and such modifications are intended to be encompassed by the ensuing claims.

What is claimed is:

1. Apparatus for differentiating a sub-population of blood cells from other blood cells and particles in a blood sample, said apparatus comprising:
    (a) an optical flow cell through which the individual blood cells and particles of a blood sample can be made to pass, one at a time;
    (b) a light source for directing a beam of radiation along an optical axis to irradiate individual blood cells and particles passing through said the optical flow cell;
    (c) a first optical detector positioned at a location to detect back-scattered radiation from an irradiated particle passing through said optical flow cell and for producing a first electrical signal proportional to the level of back-scattered radiation detected, said first optical detector comprising: (i) a photodetector; (ii) a plurality of optical fibers, each fiber having a light-collection end, an opposing light-discharge end, and an intervening light-transport region for transmitting, by multiple internal reflections, light collected by said light-collecting end to said light-discharge end, said light-discharge end being positioned proximate a light-sensitive face of said photodetector; and (iii) a fiber optic holder for positioning the respective light-collecting ends of said optical fibers at a location to collect said back-scattered radiation from an irradiated blood cell or particle;
    (d) a second optical detector positioned at a location to detect a loss of light in said light beam caused by the presence of a blood cell or particle in said light beam and for producing a second electrical signal proportional to the detected level of said light loss, said second optical detector comprising a light-diffusing element positioned on said optical axis to diffuse said light beam after irradiating said blood cells and particles passing through said optical flow cell, whereby any beam reflections occurring after blood cell or particle irradiation that would otherwise interfere with the detection of back-scattered radiation is minimized; and
    (e) a logic and control unit for receiving said first and second electrical signals and for differentiating said sub-population of blood cells from said other blood cells and particles based on the first and second electrical signals received.

2. The apparatus as defined by claim 1 wherein said fiber optic holder is designed to support a linear portion of each fiber in the vicinity of its light collecting end so that each light-collecting fiber end receives back-scattered light from irradiated particles within substantially the same angular range.

3. The apparatus as defined by claim 2 wherein said back-scatter is measured at a nominal back-scatter angle between about 7 degrees and 24 degrees, plus or minus 1 degree.

4. The apparatus as defined by claim 2 wherein the respective axes of said supported linear portions of the optical fibers extend parallel to said optical axis of said particle-irradiating beam.

5. The apparatus as defined by claim 2 wherein the respective axes of said supported linear portions of the optical fibers converge at or near an anticipated location of light-scattering blood cells and particles relative to said light-collecting ends of said optical fibers.

6. The apparatus as defined by claim 1 wherein said light-collecting ends of said optical fibers are arranged in a circular pattern centered about said optical axis.

7. The apparatus as defined by claim 1 further comprising a third optical detector that operates to sense another optical effect resulting from the irradiation of the blood cells and particles by said beam of radiation.

8. The apparatus as defined by claim 7 wherein said other optical effect is the intensity level of forwardly scattered radiation within a predetermined angular range.

9. The apparatus as defined by claim 8 wherein said predetermined angular range is about 11 degrees, plus or minus about 1 degree.

10. The apparatus as defined by claim 8 wherein said predetermined angular range is about 16 degrees, plus or minus about 1 degree.

11. The apparatus as defined by claim 7 wherein said other optical effect is the intensity level of side-scattered radiation.

12. The apparatus as defined by claim 7 wherein said third optical detector comprises:

(a) a plurality of elongated optical fibers, each operating to resolve light at a light-collecting end thereof and to transmit such light, via multiple internal reflections, to an opposing light-discharge end at which the transmitted light is discharged, each of said optical fibers having a central optical axis extending longitudinally through said optical fibers;

(b) at least one photodetector positioned adjacent to the respective light-discharge ends of said optical fibers to receive and detect discharged light; and (c) an optical fiber holder for supporting a portion of each optical fiber in the vicinity of its respective light-collecting end so that the respective optical axes of the supported fiber portions converge toward the apparent position of blood cells and particles irradiated by said beam of radiation.

13. Apparatus as defined by claim 12 wherein said optical fiber holder comprises a fiber-retaining plate having a concave surface through which a plurality of bore holes are formed in said plate for supporting said fiber portions.

14. The apparatus as defined by claim 1 further comprising a third detector that operates to sense a change in an electrical current flowing through said flow cell as occasioned by the passage of blood cells and particles through said flow cell.

15. The apparatus as defined by claim 1 wherein said second optical detector comprises a housing defining an elongated bore hole through which said beam of radiation passes prior to becoming diffused by said light diffusing element, said bore hole serving to prevent any substantial amount of diffused radiation from being detected by said first optical detector.

* * * * *